(12) United States Patent
Tomé et al.

(10) Patent No.: US 7,551,717 B2
(45) Date of Patent: Jun. 23, 2009

(54) VIRTUAL 4D TREATMENT SUITE

(75) Inventors: Wolfgang Axel Tomé, Madison, WI (US); Eric Drew Ehler, Madison, WI (US)

(73) Assignees: Wisconsin Alumni Research Foundation, Madison, WI (US); Koninklijke Philips Electronics NV, Eindhoven (NL)

( * ) Notice: Subject to any disclaimer, the term of this patent is extended or adjusted under 35 U.S.C. 154(b) by 0 days.

(21) Appl. No.: 11/894,378

(22) Filed: Aug. 21, 2007

(65) Prior Publication Data

US 2009/0052623 A1 Feb. 26, 2009

(51) Int. Cl.
*A61N 5/10* (2006.01)
(52) U.S. Cl. .......................... 378/65; 378/95
(58) Field of Classification Search .................. 378/65, 378/68, 69, 95
See application file for complete search history.

(56) References Cited

U.S. PATENT DOCUMENTS

| | | | |
|---|---|---|---|
| 2006/0274061 | A1 | 12/2006 | Wang et al. |
| 2006/0291621 | A1 | 12/2006 | Yan et al. |
| 2007/0041494 | A1 | 2/2007 | Ruchala et al. |
| 2007/0076846 | A1 | 4/2007 | Ruchala et al. |

*Primary Examiner*—Jurie Yun
(74) *Attorney, Agent, or Firm*—Shumaker & Sieffert, P.A.

(57) ABSTRACT

A virtual 4D treatment suite includes a dose calculation module, a gating module, and a dose rate adjustment module. The 4D treatment suite may be used to virtually analyze the impact the motion of a target tissue has on therapy for a particular patient and a proposed treatment plan. For example, for a proposed treatment plan, the dose calculation module may calculate a dose that would be received by a target tissue and an associated dose temporal variation based on an identified movement of the target tissue relative to at least a portion of a treatment field. Based on the calculated expected therapy dose and dose temporal variation, the gating module may determine whether to implement a gating technique for the proposed treatment plan and/or the dose rate adjustment module may determine whether to adjust the dose rate of the proposed treatment plan.

26 Claims, 7 Drawing Sheets

VIRTUAL 4D TREATMENT SUITE

STATEMENT OF GOVERNMENT INTEREST

This invention was made with United States government support awarded by the following agency under the following contract:

NIH CA109656

The United States government has certain rights in this invention.

TECHNICAL FIELD

The invention relates to radiation therapy, and more specifically to treatment planning for radiation therapy.

BACKGROUND

Radiation therapy may be used to treat a patient condition, such as cancer. For example, radiation therapy may be used to deliver ionizing radiation to a malignant tumor or other target tissue of the patient in order to control malignant or other abnormal cells. One or more external treatment beams, e.g., photon streams emitted by a radiation source, may be used to deliver the radiation to the target tissue of the patient. The area of the body through which an external radiation beam is directed to reach a tumor or other target tissue within the patient may be referred to as a "treatment field." Each treatment beam may be controlled to minimize the radiation dose delivered to normal tissue surrounding the target tissue. If a critical structure (e.g., a radiation-sensitive organ or other radiation-sensitive tissue) is located proximate to the target tissue, each treatment beam may be configured to avoid the critical structure. For example, in some radiation therapy systems, the treatment beam or multiple treatment beam angles may be arranged and weighted to define a treatment field that encompasses the target tissue, while minimizing the number of critical structures within the treatment field.

Intensity modulated radiation therapy (IMRT) is one technique for reducing the radiation dose that is delivered to critical structures that lie within a treatment field of the radiation beam. In a modulated treatment field, some portions of the treatment field (i.e., subfields) receive higher doses than others. In some cases, a high dose gradient between subfields of unequal dose may be required to avoid a critical structure while still delivering a significant dose to the target tissue. A modulation device, such as a multileaf collimator (MLC), may be used to deliver specified doses to the treatment field and/or defined subfields of the treatment field.

A MLC includes a plurality of individually adjustable leaves positioned between a radiation source and a patient. Each of the leaves may be moved in and out of the path of the treatment beam to direct the treatment beam toward the patient and shape the beam to conform to the treatment field or a subfield of the treatment field previously defined by a treatment plan. The configuration of the MLC leaves may be changed throughout therapy delivery, e.g., during a radiation therapy delivery session, and a sequence of MLC configurations may be used to deliver varying radiation dosages to subfields defined by the MLC configurations.

Depending upon the location of the target tissue within the patient, the target tissue may undergo motion during delivery of the treatment beam. For example, tumors in the lungs, stomach, pancreas or liver may move in and out of the treatment field and/or defined subfields of the treatment field due to breathing-induced motion.

SUMMARY

A virtual four-dimensional (4D) treatment suite for evaluating a proposed radiation therapy treatment plan includes, among other things, a dose calculation module, a gating module, and a dose rate adjustment module. The virtual 4D treatment suite may enable a medical practitioner to evaluate the dosimetric effects of tumor motion. The effects of the organ motion may be predicted via the dose calculation module, which calculates a predicted or expected dose of radiation received by a target tissue defined by an oncologist or other trained medical practitioner, and in some cases, critical structures near the target tissue, based on the proposed treatment plan and predicted movement of the target tissue relative to a treatment field or subfield of the treatment field. Organ motion refers to the motion of one or more organs or other tissues with respect to another structure (e.g. bony anatomy) or a coordinate system, and is not necessarily limited to motion of an organ. The dose calculation module also determines possible variation in the dose received by the target tissue, which is attributable to the predicted movement of the target tissue. The treatment planning system calculates radiation interaction and energy deposition in matter (e.g. by convolution/superposition principle, pencil beam algorithm, or Monte Carlo simulation), and the dose calculation module uses the results of such calculations in combination with target tissue motion information to calculate, by computer simulation, the dosimetric effects of motion.

The virtual 4D treatment suite provides a medical practitioner with different dose management techniques. For example, the gating module may be used to virtually determine whether a gating technique would be an acceptable or advantageous method for a particular treatment. In one embodiment, a medical practitioner may interact with the gating module to set a gating window, and the dose calculation module may calculate a resulting radiation dose and temporal dose variation based on the gating window. With the virtual environment provided by the gating module, a gating window may be evaluated by computer simulation prior to actually exposing a patient to radiation and the impact of the gating window may be studied without requiring the presence of the patient. In some embodiments, the gating module may automatically determine whether gating is useful for a particular patient and automatically set a gating window. In other embodiments, the gating module may recommend a gating window and the practitioner may accept or adjust the gating window to achieve the desired radiation temporal dose variation, e.g., to minimize the temporal variation in radiation dose while maintaining an acceptable radiation delivery time.

The dose rate adjustment module, automatically or with interaction from the practitioner, may virtually determine whether a dose rate adjustment is useful for a particular patient. Dose rate is the radiation dose delivered per unit time. In some cases, the dose rate adjustment module may decrease the radiation dose rate and increase the time of delivery to deliver substantially the same amount of radiation dose to a patient compared to a relatively greater dose rate and associated shorter delivery time. However, the decreased dose rate over a longer amount of time may help decrease possible temporal variation in radiation dose for two or more therapy sessions (or "fractions") of the treatment plan. In other cases, the dose rate adjustment module may increase the radiation dose rate and decrease the time of delivery, while delivering substantially the same radiation dose to the patient. Increasing the radiation dose rate and decreasing the delivery time may help decrease the total therapy session duration or allow for other subfield delivery times to increase while keeping a nearly constant total treatment time. As with the gating module, the dose rate adjustment module is useful for virtually determining the dosimetric effects a given dose rate adjustment may have on a proposed treatment plan prior to actually exposing the patient to radiation therapy.

In one embodiment, the invention is directed to a method comprising identifying relative motion between a region of interest of a patient and at least a portion of a treatment field defined by a proposed treatment plan, calculating an expected therapy dose and an associated temporal variation in the expected therapy dose to be delivered to the region of interest for the proposed treatment plan based on the identified relative motion between the region of interest and the at least the portion of the treatment field, and determining whether to apply a dose management technique to the proposed treatment plan based on the expected therapy dose and the associated temporal variation in the expected therapy dose.

In another embodiment, the invention is directed to a system comprising a dose calculation module and a dose management module. The dose calculation module calculates an expected therapy dose and an associated temporal variation in the expected therapy dose to be delivered to a region of interest for a proposed radiation therapy treatment plan for a patient based on an identified relative motion between the region of interest and at least a portion of a treatment field. The dose management module determines whether to implement a dose management technique based on the expected therapy dose and the associated temporal variation in the expected therapy dose.

In another embodiment, the invention is directed to a computer-readable medium containing instructions. The instructions cause a programmable processor to identify relative motion between a region of interest and at least a portion of a treatment field defined by a proposed treatment plan, calculate an expected therapy dose and an associated temporal variation in the expected therapy dose to be delivered to the region of interest for the proposed treatment plan based on the identified relative motion between the region of interest and the at least the portion of the treatment field, and determine whether to apply a dose management technique to the proposed treatment plan based on the expected therapy dose and the associated temporal variation in the expected therapy dose.

In another embodiment, the invention is directed to a system comprising means for identifying relative motion between a region of interest of a patient and at least a portion of a treatment field defined by a proposed treatment plan, means for calculating an expected therapy dose and an associated temporal variation in the expected therapy dose to be delivered to the region of interest for the proposed treatment plan based on the identified relative motion between the region of interest and the at least the portion of the treatment field, and means for determining whether to apply a dose management technique to the proposed treatment plan based on the expected therapy dose and the associated temporal variation in the expected therapy dose.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
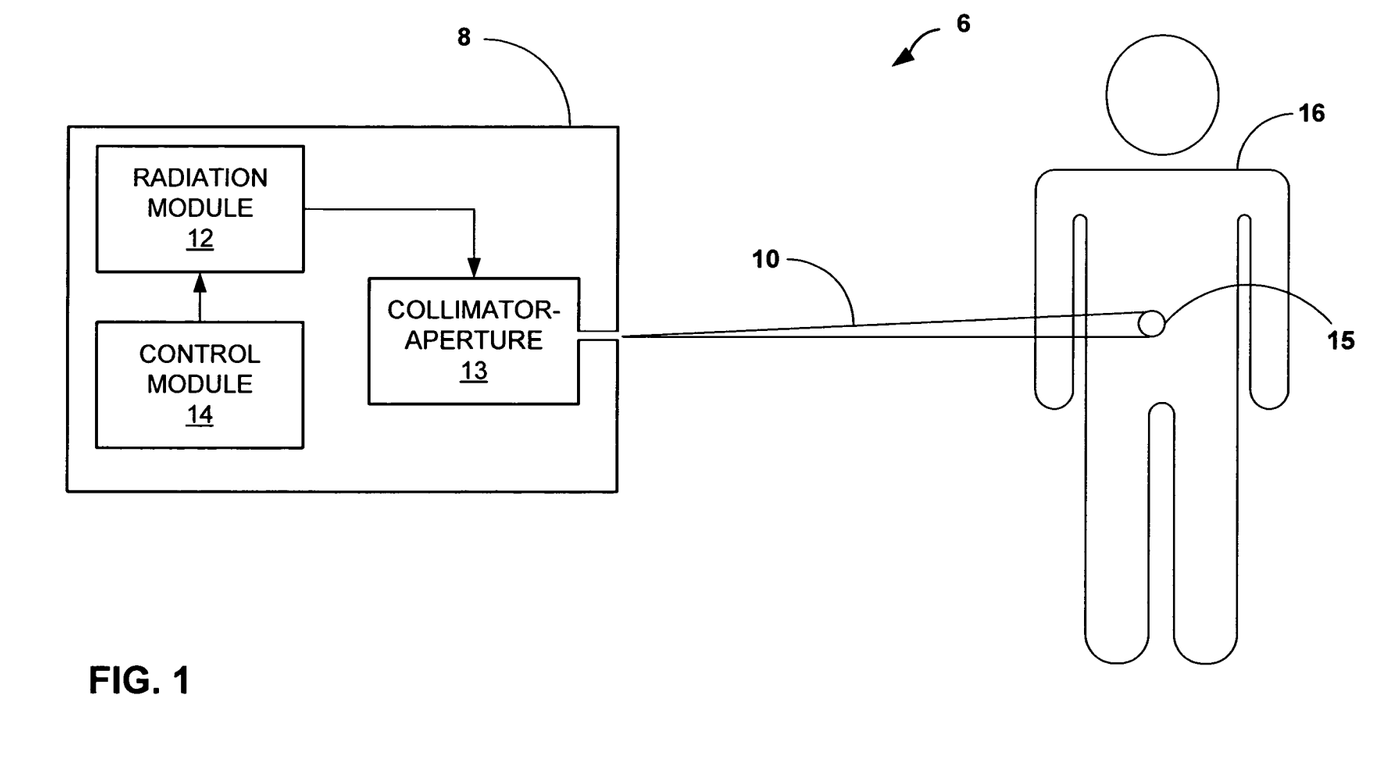
FIG. 1 is a schematic diagram of a radiation therapy system.

FIG. 1 is a schematic drawing of a radiation therapy system 6. Radiation therapy system 6 includes a radiation system 8, which can generate a radiation beam 10. In FIG. 1, beam 10 is directed at treatment field 15, which is an area of the body of patient 16 that beam 10 is directed at in order to reach a target tissue, i.e., the tissue to be treated by beam 10, within patient 16. The target tissue may be, for example, malignant cells or other abnormal tissue. Radiation system 8 includes radiation module 12, which includes a radiation source (e.g., a linear accelerator or gamma ray source), which generates beam 10.

Radiation system 8 may also include a collimator-aperture module 13 to shape and direct beam 10 toward patient 16. For example, the collimator-aperture module 13 may direct beam 10 toward a target tissue and/or away from a critical structure within patient 16. Control module 14 controls radiation module 12 either directly or indirectly in order to control various characteristics of beam 10, such as, but not limited to, the intensity of beam 10 and the duration beam 10 is on, which may affect the radiation dose received by patient 16. Control module 14 may customize the dose rate used for radiation delivery of different subfields, i.e., defined portions of treatment field 15. Control module 14 may include a user interface for radiation system 8 (e.g. a control panel for a linear accelerator) as well as software and computation devices of radiation system 8 used to execute a given treatment plan.

As described in further detail below, the desired characteristics of beam 10, such as the intensity of beam 10 and/or the duration beam 10 is turned on, may be determined with the aid of a virtual four-dimensional (4D) treatment suite. The beam characteristics and other data from the virtual 4D treatment suite may then be inputted to the control module 14 manually or automatically via the virtual 4D treatment suite, a treatment planning system or another computing device. For example, data from the virtual 4D treatment suite may be inputted into control module 14 of radiation system 8. As one example, if the virtual 4D treatment suite determines dose rates to use during therapy delivery, the dose rate data may be inputted into control module 14. Control module 14 may send the dose rate data (e.g., as binary data or an electrical signal) a dose rate controller (e.g., a dose rate servo) to control the dose rate of radiation module 12.

In one embodiment, the collimator-aperture module 13 may, but need not, include a multileaf collimator (MLC) with a plurality of individually adjustable leaves that may be controlled by a computing device. As described in further detail below with reference to FIG. 2, which illustrates an example MLC, adjustment of the MLC leaves may change the shape of radiation beam 10, and in particular, may focus the radiation beam 10 on certain areas of patient 16 and block beam 10 from reaching other areas. The use of various MLC configurations during therapy delivery to a target tissue may result in a modulated dose profile. In other embodiments, beam modulation blocks may filter portions of beam 10 to vary the intensity of beam 10 over the target tissue of patient 16. The use of MLC configurations, beam modulation blocks, or other beam intensity modulation devices may control the distribution of the radiation dose (i.e., the "dose distribution") delivered by radiation module 12 to conform around the target tissue and reduce the dose to normal structures and tissues, such as normal tissues that surround the target tissue.

Prior to treatment with radiation therapy system 6, a 4D image data set (i.e., a time based series of three-dimensional image data sets of an anatomical structure) of patient 16 may be obtained (e.g., using magnetic resonance (MR) or computed tomography (CT) imaging techniques) for treatment planning purposes. An oncologist or other trained practitioner may identify the location of a tumor or other target tissue using at least a portion of a 4D data set (e.g., data corresponding to a single 3D image or the entire 4D data set). Critical structures that are important for radiation beam 10 to avoid may also be identified with at least a portion of the 4D data set. The target tissue and/or critical structures, which may be defined by an oncologist or other trained practitioner, may be referred to as regions of interest (ROIs). Based on the locations of the ROIs, a treatment planning system may be used to determine which MLC configurations to integrate into a treatment plan for patient 16 in order to deliver therapy to the target tissue while avoiding radiation delivery to the critical structures. A treatment plan for patient 16 includes, among other things, the orientation of radiation beam 10 with respect to patient 16, the radiation dose to be delivered to patient 16 during a treatment session and the MLC 18 configuration(s). The treatment planning system may also determine the dose that will be delivered from beam 10 for each MLC configuration.

The treatment plan may be developed using any suitable technique, such as with commercially available treatment planning system software (e.g., Pinnacle$^3$, which is commercially available from Philips Medical Systems of Bothell, Wash., PrecisePLAN®, which is commercially available from Elekta AB of Stockholm, Sweden, and Eclipse, which is commercially available from Varian Medical Systems, Inc. of Palo Alto, Calif.). The treatment plan may also set forth the number of treatment sessions. In some cases, radiation therapy is delivered via multiple treatment sessions, referred to as fractions, spread out over time. The time between fractions reduces the toxicity to normal tissue from radiation exposure. For example, a treatment plan may include one fraction per day five days per week for a four to eight week period. Each fraction of a treatment plan may, but need not, include the same sequence of MLC configurations. The dose delivered to the target tissue may be substantially the same during each fraction (e.g., 1.5 to 2.75 Gray per fraction). The effectiveness of the radiation treatment may be increased by providing substantially the same radiation dose to the target tissue during each fraction. Delivering substantially the same radiation dose to the target tissue during each fraction may aid in minimizing temporal dose variation to any area of the target tissue. The temporal dose uniformity may be improved by providing substantially the same radiation dose to the target tissue each time an individual MLC configuration is used.

Figure 2:
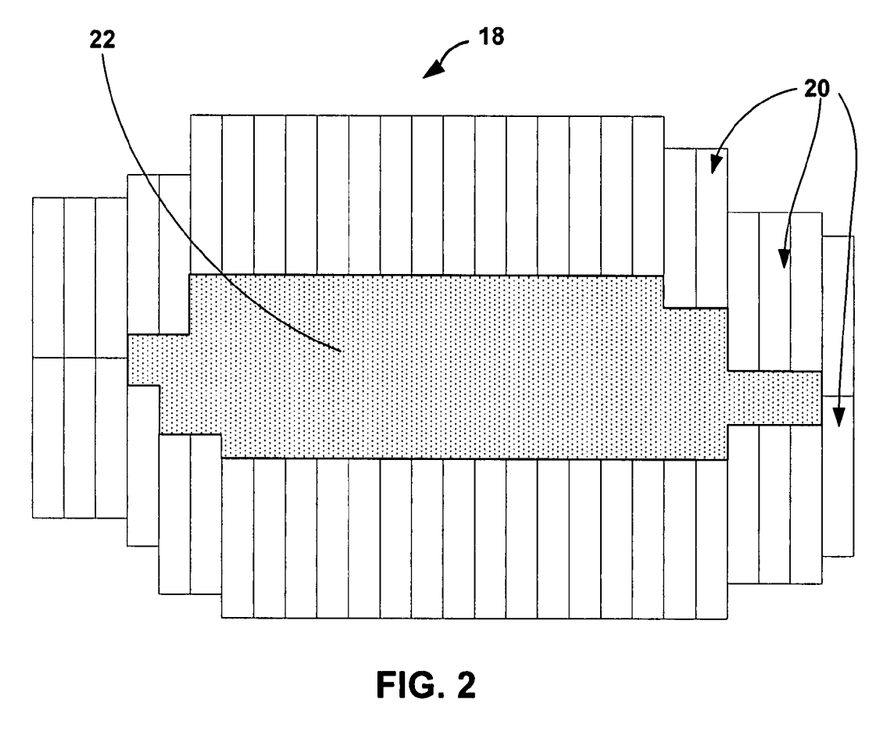
FIG. 2 is a schematic view of an example multileaf collimator (MLC).

FIG. 2 is a schematic view of an example MLC 18. MLC 18 includes a plurality of leaves 20. Each of the leaves 20 may be moved into or out of the path of treatment beam 10 (FIG. 1) to direct treatment beam 10 toward patient 16. For example, MLC 18 may be positioned between radiation module 12 and treatment field 15 (FIG. 1) of patient 16 in order to conform treatment beam 10 to the shape of region 22 defined by the positions of the MLC leaves 20. Region 22 may conform to treatment field 15 or a subfield of treatment field 15. That is, leaves 20 of MLC 18 may be adjusted to allow radiation to be delivered to a portion of treatment field 15, i.e., a subfield. For purposes of example, subfields will be described herein with respect to therapy delivery. However, the invention is not so limited and may include radiation delivery to the entire treatment field 15 (e.g., through use of a MLC configuration that conforms to treatment field 15).

The configuration of leaves 20 may be changed throughout a therapy delivery session, as well as between therapy delivery sessions to aid in delivering a significant radiation dose to the target tissue while minimizing the radiation delivered to normal tissue and/or a critical structure identified by a medical practitioner. For example, in some cases, a sequence of multiple MLC leave 20 configurations may be used throughout a treatment session, and a radiation beam 10 having a specified dose may be delivered to patient 16 for each MLC configuration.

Temporal variation in the radiation dose absorbed by the target tissue may occur due to the motion of the MLC leaves 20 with respect to the motion of the target tissue, which is referred to as the interplay effect. The target tissue may undergo motion induced by respiration, peristalsis, or some other physiologic process during delivery of treatment beam 10, causing the target tissue or critical structures to move in and out of the subfields defined by the MLC 18 configurations. The temporal variation in the radiation dose may be affected by the relative motion between the target tissue and the subfields defined by the MLC 18 configurations. For example, depending on the position of the moving target tissue at the time beam 10 is activated to deliver therapy to the target tissue, there may be a possibility of delivering the dose to a subfield when the target tissue is not within the treated subfield.

According to the systems and methods for evaluating a proposed treatment plan described herein, 4D data of the relevant anatomical structure and relevant movement data may be used to determine whether it is useful to apply (i.e., implement) a dose management technique. The movement data includes data relating to the movement of the anatomical structure or other tissue that contributes to the movement of the ROI over time. The type of movement data that is relevant depends upon the location of the ROI. For example, in the case of an ROI that moves due to patient breathing, the relevant movement data includes patient breathing data, which may be time-based data indicating the breathing phase of patient 16. Breathing data may be, for example, an electrical signal generated from a pressure transducer indicating motion of the patient's lungs.

The virtual 4D treatment suite may determine dosimetric effects of ROI motion relative to treatment field 15 or subfields of treatment field 15 based on the proposed treatment plan, 4D image data (e.g., the 4D image taken for treatment planning purposes), and target tissue movement data (e.g., breathing data for patient 16). Based on the identified motion of the ROIs, the 4D treatment suite or a medical practitioner interacting with the treatment suite may determine whether to apply a dose management technique. For example, a dose management technique may be applied to reduce the possible temporal variation in dose that is attributable to the movement of the target tissue relative to the treatment field 15 or a subfield of the treatment field 15. Examples of dose management techniques include gating and dose rate adjustment, which are described in further detail below. The proposed treatment plan may be generated using a treatment planning system as described in further detail above.

Figure 3:
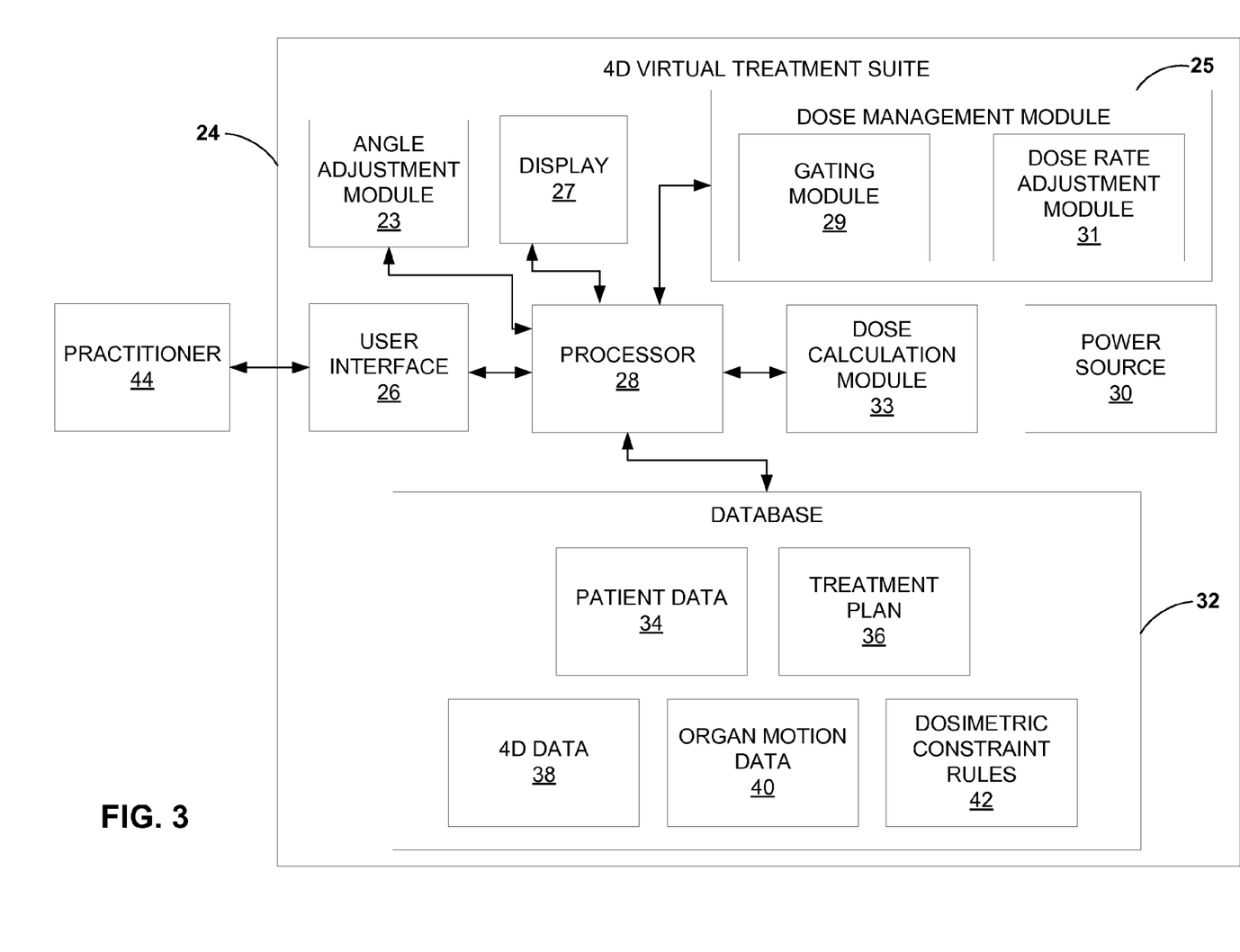
FIG. 3 is a block diagram illustrating an example embodiment of a virtual four-dimensional (4D) treatment suite.

FIG. 3 is a block diagram illustrating an example embodiment of a virtual 4D treatment suite 24 that may be used to predict the effects of a proposed treatment plan. In general, 4D treatment suite 24 may be implemented via hardware, software, firmware or a combination thereof. For example, in one embodiment, suite 24 may comprise a computer-readable medium comprising instructions for processor 28. In some exemplary embodiments, 4D treatment suite 24 may be implemented within a general purpose computing environment such as a personal computer, workstation, or dedicated dose management control unit, each comprising one or more processors. In the illustrated embodiment, virtual 4D treatment suite 24 includes angle adjustment module 23, dose management module 25, user interface 26, processor 28, power source 30, database 32, and dose calculation module 33. Dose management module 25 includes gating module 29 and dose rate adjustment module 31. Various modules 23, 25, and 33 may be implemented as programmable features, applications or processes of processor 28, or implemented via other processors or hardware units. Furthermore, modules 23, 25, and 33 may be implemented in hardware, software, and/or firmware, or any combination thereof.

Database 32 includes patient data 34, treatment plan 36, 4D data 38, organ motion data 40, and dosimetric constraint rules 42. Database 32 may be stored in one or more data storage media. Suite 25 may include memory for use by processor 28 or other processor or hardware units in performing a variety of the function described in this disclosure. Practitioner 44 may interact with virtual 4D treatment suite 24 via user interface 26, which may include, for example, a keyboard, buttons, touch screen, joystick, mouse or another peripheral pointing device. In some embodiments, virtual 4D treatment suite 24 may be at least partially implemented via software executing on a computing device. For example, a computing device may include user interface 26, display 27, processor 28, power source 30, and database 32, while software executing on the computing device may provide dose management module 25 and dose calculation module 33. In some embodiments, virtual 4D treatment suite 24 may be a stand alone device, while in other embodiments, virtual 4D treatment suite 24 may be implemented into a computing device that is common to two or more applications.

Database 32 stores data relevant to the operation of virtual 4D treatment suite 24. For example, database 32 may store patient data 34 including general information, such as a name, birth date, and a medical history for patient 16. Optionally, patient data 34 may include appointment scheduling information and billing information. Database 32 may also include treatment plan 36, which includes MLC configurations and dose information for patient 16, 4D data 38 obtained from a 4D image of patient 16, and organ motion data 40 that may be associated with the 4D data 38. Organ motion data 40 may be obtained via any suitable technique, such as by tracking internal or external markers (e.g., radio opaque markers implanted in the lung or on the patient's chest) that are positioned near the target tissue. As another example, a respiration belt or a spirometer, which each output an electrical signal that varies as a function of respiration of patient 16, may monitor the breathing activity of patient 16 to generate organ motion data 40. In yet another example, organ motion data 40 may be obtained from radiofrequency emitting markers (e.g. Calypso® 4D Localization System, available from Calypso Medical Technologies of Seattle, Wash.), which are placed internally in the patient near or within the ROI. The coordinates of the markers may be determined based on the radiofrequency signal emitted by the markers.

Organ motion data 40 may be stored to create a library of organ motion data during each radiation therapy delivery session (i.e., fraction) for a part or the entire treatment course. Organ motion data 40 may also contain, as a subset, organ motion reproducibility data. Organ motion reproducibility data may represent possible variations in organ motion and may provide a sense of how well the recorded organ motion data 40 represents these possible variations. Organ motion reproducibility data may be reflective of variation in organ motion data 40 due to, for example, changes in breathing rate (e.g., a patient may not breath at the same breathing rate at all times). Generally, organ motion data 40 may be periodic. For example, organ motion data 40 may vary with a patient's respiration, peristalsis, or some other cyclic physiological process such that a phase of the cyclic (e.g., periodic) physiological process generally corresponds to a position of the organ. Organ motion reproducibility data may be indicative of how organ motion data 40 varies from period to period. For example, if the frequency and/or magnitude of the cyclic physiological process changes (e.g., the patient's breathing rate or deepness of breath changes), organ motion data may also change. Organ motion reproducibility data may be acquired before the start of the radiation therapy to predict an expected dose and associated temporal dose variation. For example, the virtual 4D treatment suite may use organ motion reproducibility data when determining possible temporal dose variation. Additionally or alternatively, organ motion reproducibility data may be acquired during radiation therapy treatment delivery and virtual simulations may be performed based on detected organ motion reproducibility error to determine how temporal dose variation is effected.

In other embodiments, organ motion reproducibility parameters (e.g. a mean breathing rate and associated standard deviation) based on patient, institutional, or population based statistics, or a random estimation of organ motion based on a random number generator and patient, institutional, or population based statistics, may be used by the virtual 4D treatment suite to determine how changes in the organ motion may affect expected dose and temporal dose variation.

Additionally, database 32 may include dosimetric constraint rules 42, such as ranges of allowable values for radiation dose to normal tissue, inter-fractional dose uniformity, intra-fractional dose uniformity, and/or delivery time. Dosimetric constraint rules 42 may be specific to a particular patient 16 or practitioner 44 or may be common to one or more patients or practitioners. As will be described in further detail below, processor 28 may use data from database 32 in combination with user input from user interface 26 to aid in determining whether any dose management techniques should be implemented with proposed treatment plan 36, e.g., whether proposed treatment plan 36 should be gated and/or whether a dose rate of proposed treatment plan 36 should be adjusted.

Angle adjustment module 23 may be used to adjust the orientation of the MLC 18 leaves 20 with respect to patient 16, e.g., in order to modify the angle at which beam 10 (FIG. 1) is oriented with respect to patient 16. Since the MLC leaves 20 have a finite shape, one angle may allow beam 10 (FIG. 1) to more uniformly irradiate target tissue 50 while avoiding critical structures compared to other possible angle settings. Practitioner 44, via user interface 26, may request angle adjustment module 23 to make an angle adjustment or angle adjustment module 23 may automatically adjust the angle of beam 10 in order to optimize the dose distribution and/or the temporal dose variation to target tissue 50 and/or to avoid critical structures. For example, dose calculation module 33 may calculate an expected therapy dose to be delivered to target tissue 50 and/or a critical structure and associated temporal dose variation based on the angle setting, and angle adjustment module 23 may adjust the angle setting based on the expected dose and temporal dose variation.

Figure 4A:
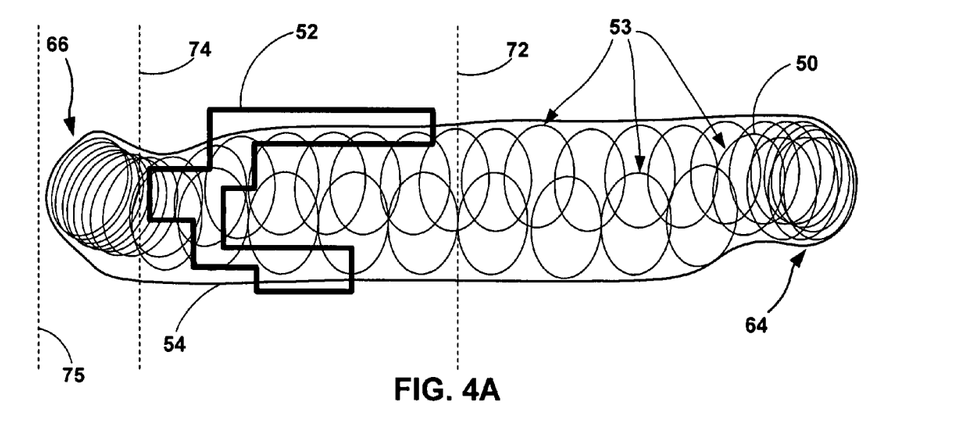
FIG. 4A is a schematic diagram that illustrates the motion of a target tissue relative to a treatment subfield defined by an example MLC configuration.

Processor 28 may identify relative motion between target tissue 50 and subfield 52 defined by an example MLC 18 configuration. For example, processor 28 may use the proposed treatment plan 36, 4D image data 38, and organ motion data 40 stored within database 32 to generate a depiction of the motion of target tissue 50 relative to a treatment field or subfield 52 defined by a MLC configuration of treatment plan 36. In some embodiments, processor 28 presents the simulated movement to practitioner 44 via display 27. A simulation motion of target tissue 50 is schematically shown in FIG. 4A. In one embodiment, the simulated motion is provided in a Beam's Eye View (BEV) plane, i.e., from the perspective of beam 10 (FIG. 1), with the center of the beam as the (0,0) coordinate. The BEV may differ depending on the gantry, collimator, or couch angle or any other orientation modifier, e.g., the position of the device that rotates radiation module 12 or rotates relative to radiation module 12 of radiation therapy system 6 (FIG. 1).

The motion of target tissue 50 may be simulated using any suitable technique. In one embodiment, the coordinates of the center of target tissue 50 during a full range of motion may be obtained from a treatment planning software program. Alternatively, processor 28 may assign a coordinate system to target tissue 50 and generate the relevant coordinates that indicate the range of motion of target tissue 50 based on 4D data 38 and/or organ motion data 40 that provides an indication of the target tissue movement. The coordinate data may be provided in two dimensions or three or more dimensions. The target tissue coordinate data may be saved with 4D data 38 and organ motion data 40 in database 32, e.g., as a text file (.txt), a script file (.m), or any other appropriate format. Processor 28 may simulate target tissue 50 movement using the coordinates.

Figure 4B:
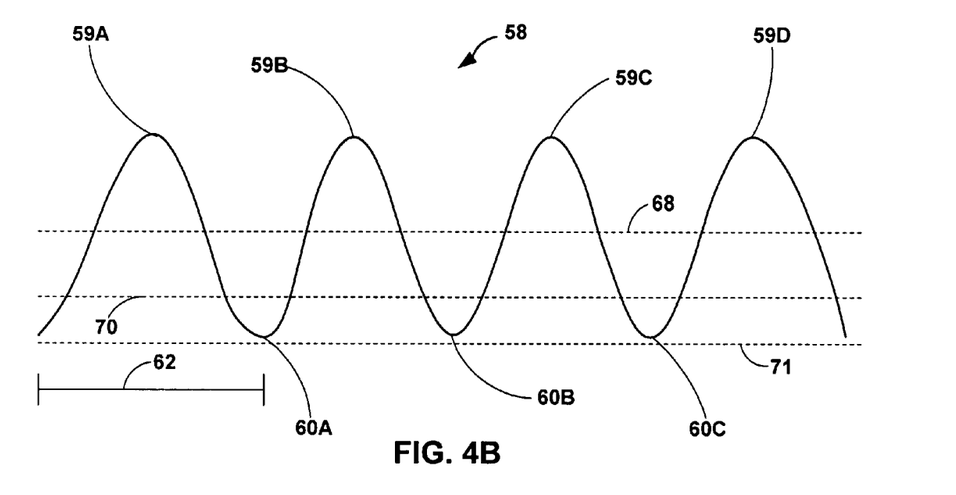
FIG. 4B is an example graph of a patient's breathing pattern associated with the target tissue's motion envelope.

FIG. 4A illustrates a simulated movement of target tissue 50 relative to treatment subfield 52, which defines a motion envelope 54, and FIG. 4B illustrates corresponding breathing pattern 58. In FIG. 4A, the probability density function of the target tissue's motion throughout the breathing period is illustrated. Each circle 53 represents a position of target tissue 50 during a given time interval (e.g., one breathing cycle). Target tissue 50 spends more time in the regions with a higher density of circles, such as region 64. Motion envelope 54 outlines the extent of the target tissue's motion.

Based on the motion of target tissue 50 relative to subfield 52 of treatment field 15 (FIG. 1), dose calculation module 33, under the control of processor 28, may calculate an expected therapy dose, e.g., an expected mean dose, and associated temporal dose variation that would be delivered to target tissue 50 and/or other ROIs defined by treatment plan 36 during therapy delivery. In some embodiments, dose calculation module 33 may use a biological model to calculate the biological effect on patient 16. For example, dose calculation module 33 may determine a normalized total dose and/or a biologically equivalent dose.

Dose calculation module 33 may also calculate possible variations in expected therapy dose that would be delivered to target tissue 50 based on how target tissue 50 moves relative to subfield 52, the delivery time (i.e., the duration of the radiation delivery) specified by treatment plan 36, and the position of target tissue 50 with respect to subfield 52 when therapy delivery is started. For example, dose calculation module 33 may determine a range of possible doses received by target tissue 50 for a plurality of delivery times, dose rates, gating windows, or other parameters that may affect the temporal dose variation.

Dose calculation module 33, under the control of processor 28, may present the expected therapy dose and associated temporal dose variation values to practitioner 44 via display 27. Practitioner 44 may analyze the temporal dose variation values to determine if gating may be beneficial during delivery of radiation to subfield 52. For example, gating may be beneficial to reduce the temporal variation in dose during a treatment session and/or between treatment sessions. Alternatively, dose calculation module 33 may analyze the temporal dose variation values and provide a gating recommendation to practitioner 44. For example, dose calculation module 33 may provide an indication via display 27 to practitioner 44 that gating is recommended or not recommended.

In one embodiment, dose calculation module 33 generates one or more histograms that indicate the frequency of results from computer simulation, such as the expected dose per fraction, the expected total dose, and/or temporal dose variation, for a proposed treatment plan 36 and presents the histograms to practitioner 44 via display 27.

Figure 5:
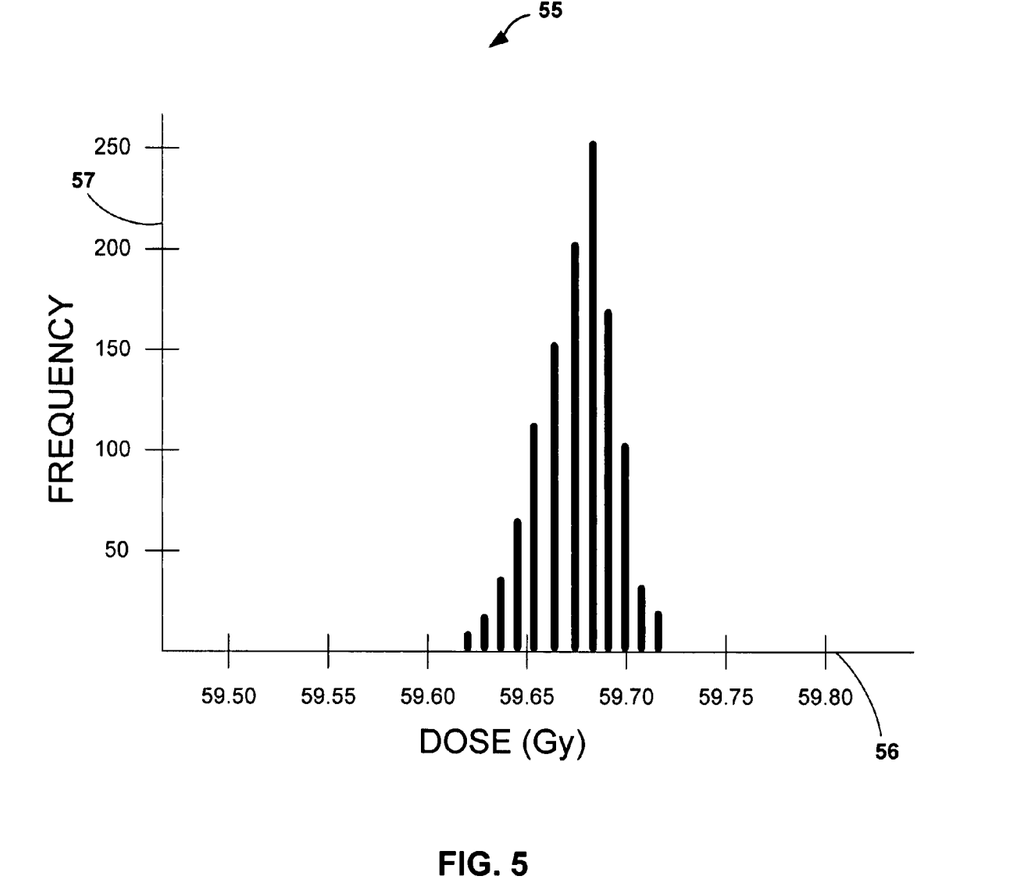
FIG. 5 illustrates an example histogram generated by a dose calculation module of the virtual 4D treatment suite based on a treatment plan and a relative motion between a target tissue and a subfield of a treatment field.

FIG. 5 illustrates an example histogram 55. It is possible that organ motion may not be synchronized with radiation delivery. This scenario may result in many possible variations in the expected dose and associated temporal dose because there are many possible positions that the target tissue may occupy when radiation is delivered. Therefore, computer simulation of the treatment course is performed for many trials so that an acceptable sample of the range in expected dose and associated temporal dose variation may be obtained as well as the probability of each solution. Histogram 55 illustrates an example of the expected dose to an area within the target volume for 1000 trials of a 30 fraction treatment course. The dose received is shown on x-axis 56, and the frequency (e.g., number of trials) is shown on y-axis 57. In this manner, a histogram may illustrate expected dose and associated temporal dose variation as well as the probability of each solution. Dose calculation module 33 may generate histograms for multiple gating windows or other settings and display the histograms to practitioner 44 via display 27. Displaying histograms for multiple parameter settings may allow practitioner 44 to visually analyze and compare parameter settings.

Returning now to FIG. 3, gating module 29 of dose management module 25 of virtual 4D treatment suite 24 may allow the effects of gating and gating window settings to be analyzed. Gating refers to a technique in which beam 10 is turned off when target tissue 50 displacement relative to treatment field 15 or subfield 52 exceeds a user-specified threshold and turned back on when target tissue 50 reenters the threshold. If the gating displacement threshold is less than the displacement due to breathing, the beam is turned on and off depending on the breathing phase and associated displacement of target tissue 50. The motion of the target tissue may be tracked in any suitable way, such as by tracking a marker placed on or within patient 16, a respiration belt or a spirometer or by initially synchronizing the gating windows with the patient's respiratory cycle.

If practitioner 44 or dose calculation module 33 determine that gating is desired for patient 16 based on the temporal dose variation calculated by dose calculation module 33, practitioner 44 may utilize gating module 29 of virtual 4D treatment suite 24 to set the gating window. Additionally or alternatively, gating module 29 may be useful for determining whether gating is desirable, such as by determining the effects of gating on the temporal radiation dose variation and/or delivery time compared to simulation of a non-gated radiation delivery.

FIG. 4B illustrates a graph of the patient's breathing pattern 58 associated with the target tissue's motion envelope 54. Breathing pattern 58 may be obtained from organ motion data 40 stored within virtual 4D treatment suite 24. Breathing pattern 58 may be a periodic wave with peaks 59A-59D each corresponding to a full inhale and valleys 60A-60D each corresponding to a full exhale. Breathing cycle 62 represents one breathing cycle starting and ending at a full exhale. Each phase of breathing cycle 62 may correspond to a position of target tissue 50. For example, the peak 59A of breathing cycle 62 may approximately correspond to position 64 of target tissue 50, and the valley 60A of breathing cycle 62 may approximately correspond to position 66 of target tissue 50. Since the breathing pattern is periodic, each of peaks 59A-59D may approximately correspond to position 64 of target tissue 50 and each of valleys 60A-60C may approximately correspond to position 66 of target tissue 50.

In some embodiments, gating module 29 of virtual 4D treatment suite 24 may provide the user, e.g., practitioner 44, with at least two operating modes. In a first operating mode, the user may set the gating window by selecting a portion of the breathing cycle during which radiation therapy may be delivered, e.g., via user interface 26. In a second operating mode, the user may set the gating window by selecting the desired portion of motion envelope 54, e.g., via user interface 26. In other embodiments, the virtual 4D treatment suite may only offer one of the aforementioned modes of operation.

In the operating mode in which a gating window is selected based on the patient's breathing cycle, organ motion data 40 (e.g., breathing pattern 58) may be displayed on display 27 of virtual 4D treatment suite 24, and practitioner 44 may select a portion of the breathing cycle to deliver radiation therapy. For example, practitioner 44 may interact with the display of organ motion data 40 via a user input device, such as a mouse, keyboard, joystick, touch-screen, or another peripheral pointing device. For example, in the embodiment illustrated in FIG. 4A, the most likely position for the target tissue 50 is near the exhale position, so practitioner 44 may wish to stop therapy delivery when patient 16 is inhaling. Practitioner 44 may position upper limit 68 to set a gating threshold. If, for example, upper limit 68 is chosen as an upper gating window limit, then radiation will not be delivered when the target tissue or a surrogate exceeds the threshold 68. For instance, radiation will not be delivered at points near full inhale 59. More specifically, if the phase of the patient's breathing is above upper limit 68 (i.e., between upper limit 68 and peaks 59), therapy will not be delivered.

Once the phase of the patient's breathing is below upper limit 68 (i.e., between upper limit 68 and valleys 60), therapy delivery may resume. Additionally or alternatively, practitioner 44 may select a lower threshold limit. In one embodiment the lower threshold 71 could be placed outside of the motion envelope to help ensure patient breathing reproducibility error does not cause the target tissue position to exceed the predetermined motion envelope. The lower threshold 71 may correlate with threshold 75 in FIG. 4A. In another embodiment the lower threshold limit may be placed within the motion envelope such that when the patient's breathing phase is below lower limit 70 (i.e., between lower limit 70 and valleys 60), therapy will not be delivered.

Practitioner 44 may wish to compare, by computer simulation, various gating thresholds, such as lower gating limits 70 and 71. The comparison may include such a comparison of one or more dosimetric factors, such as expected total dose to the target tissue 50, normal tissues, and/or critical structures and associated temporal dose variation. Other factors such as the expected total delivery time may also be used in the comparison.

In some embodiments, one gating window is selected for the entire treatment plan. In other embodiments, the gating window setting may be evaluated for individual subfields, which may result in different gating window settings for different subfields. For example, in the embodiment illustrated in FIGS. 4A and 4B, target tissue 50 is outside of subfield 52 when patient 16 is inhaling, so practitioner 44 may wish to stop therapy delivery to subfield 52 when patient 16 is inhaling. Practitioner 44 may position upper limit 68 to set a gating threshold for subfield 52. Additionally, in FIG. 4B, target tissue 50 is outside of subfield 52 when patient 16 fully exhales, so practitioner 44 may wish to stop therapy delivery to subfield 52 when patient 16 fully exhales. Practitioner 44 may position lower limit 70 to set a lower gating threshold for subfield 52.

In embodiments in which practitioner 44 sets the gating window by selecting a portion of the target tissue's motion envelope 54, virtual 4D treatment suite 24 may present motion envelope 54 and subfield 52 defined by a particular MLC configuration on display 27. In some cases, gating module 29 of virtual 4D treatment suite 24 determines the portion of the breathing cycle that corresponds to the selected portion of motion envelope 54. For example, upper limit 68 may approximately correspond to boundary 72 and lower limit 70 may correspond to boundary 74 on motion envelope 54. Practitioner 44 may interact with the display of the motion envelope and directly select a portion of the breathing cycle by adjusting limits 68 and/or 70 with a user input device of user interface 26. Alternatively, practitioner 44 may indirectly select a portion of the breathing cycle by adjusting boundaries 72 and/or 74 with the user input device.

Radiation dose calculation module 33 may calculate the expected therapy dose and temporal dose variation values resulting from the selected gating window setting (e.g., the window between upper limit 68 and lower limit 70). The calculated dose values may provide the expected mean dose to the target tissue and/or other ROIs for the selected gating window. Practitioner 44 (e.g., an oncologist or other practitioner) may evaluate the gating window setting based on the calculated dose values, and modify the gating window setting via gating module 29 as desired to achieve the desired dose value. For example, practitioner 44 may compare the expected therapy dose and temporal dose variation values for the selected gating window to the expected therapy dose and temporal dose variation values for non-gated therapy delivery and/or dose and temporal dose variation values for other possible gating window settings.

Other objectives and constraints may also be considered when the effects of gating and gating window settings are analyzed. For example, dose calculation module 33 may determine the dose to normal tissue, inter-fractional dose uniformity, intra-fractional dose uniformity, and/or delivery time, and practitioner 44 may weigh the different dosimetric values resulting from a treatment plan when deciding if gating will be used and/or setting the gating window. Practitioner 44 may also consider dosimetric constraint rules 42, which are stored within database 32 of virtual 4D treatment suite 24. In one embodiment, practitioner 44 inputs dosimetric constraint rules 42 into virtual 4D treatment suite 24 via user interface 26. In another embodiment, dosimetric constraint rules 42 are determined by a manufacturer of virtual 4D treatment suite 24 or by the practitioner's clinic. Dosimetric constraint rules 42 may be specific to a particular patient 16, particular practitioner 44, particular tumor type, etc. Alternatively, a common set of dosimetric constraint rules 42 may be applied to more than one patient or tumor type, used by one more than one practitioner, and so forth. Processor 28, gating module 29, and/or dose calculation module 33 may determine whether the treatment plan satisfies each of these constraints for treatment delivery without gating, as well as each of the gating window settings, if any, selected by practitioner 44.

In other embodiments, gating module 29 of virtual 4D treatment suite 24 may suggest one or more gating window settings based on dosimetric constraints 42. For example, practitioner 44 may specify that the dose delivered to the target tissue during each fraction must be within a range of plus or minus a certain percentage, e.g., between about zero to about five percent, of the prescribed dose. As another example, practitioner 44 may specify a maximum allowable delivery time. Gating module 29 may suggest one or more gating window settings that meet dosimetric constraint rules 42 inputted by practitioner 44 via user interface 26.

In general, virtual 4D treatment suite 24 provides a tool with which practitioner 44 may virtually analyze a treatment plan and determine whether gating may be beneficial to patient 16. In previous systems, the gating window is set by a practitioner when patient 16 is within the treatment suite or a radiation therapy simulator. For example, the clinician may use real-time fluoroscopy and a real-time respiratory signal to visualize how target tissue 50 moves relative to treatment field 15 and any possible sub fields as patient 16 breathes. Based on this visualization, the clinician may set the gating window. The previous systems rely on the practitioner's knowledge and judgment, which may result in a less accurate gating window setting as compared to the virtual gating setting provided by gating module 18 of virtual 4D treatment suite 24.

By virtually analyzing the effects of gating rather than using fluoroscopy, the amount of time that patient 16 must be present for treatment planning is reduced. Furthermore, the virtual analysis may help reduce the patient's radiation exposure because the virtual treatment suite may help reduce or eliminate the use of a radiation therapy simulator for some target tissues. The virtual 4D treatment suite allows for relatively in-depth quantitative analysis of the dosimetric consequences, such as the expected dose and associated temporal dose variation, of gating window settings, which provides features not available with current techniques of setting the gating window.

In another aspect of virtual 4D treatment suite 24 and methods described herein, a probability density function of the target tissue's motion throughout the breathing cycle 62 may be used to determine whether the dose rate should be adjusted for the proposed treatment plan. Typically, therapy is delivered using one dose rate (e.g., 0.05 Gray/second at 10 cm depth in water), which may be the same for all patients. However, controlling the dose rate may help ensure a relatively consistent temporal dose is delivered to target tissue 50. Dose rate adjustment may be particularly important when the target tissue motion is not synchronized with the radiation therapy delivery. When the radiation delivery is not synchronized with the target tissue motion, the radiation is delivered with the target tissue starting at a random breathing phase, which may affect the radiation dose delivered to target tissue 50. As one example, during a particular therapy fraction, the radiation delivery to treatment subfield 52 via beam 10 may be complete before target tissue 50 even enters the treatment subfield 52. In such a situation, target tissue 50 may not receive any radiation from beam 10 for this theoretical fraction. Dose rate adjustment module 31 of virtual 4D treatment suite 24 provides a tool for setting a dose rate to increase the probability that radiation is delivered to target tissue 50 regardless of the position of target tissue 50 in the breathing phase when the radiation for a given subfield is first delivered.

Depending on the configuration of the subfield (e.g., subfield 52), there may be a possibility that target tissue 50 will not occupy the irradiated subfield while the radiation is delivered, particularly when gating is not used. For example, if the subfield occupies a small portion of the target tissue's motion envelope 54 and therapy is delivered to the subfield for a fraction of the breathing cycle, target tissue 50 may not occupy the subfield when radiation is delivered to the subfield. Also, target tissue 50 may occupy the irradiated area (e.g., subfield 52) of motion envelope 54 in one fraction but not in another. Depending on when radiation is delivered, target tissue 50 may be completely missed, partially hit and missed, or completely hit by radiation beam 10. This variation may affect the expected mean dose to target tissue 50 as well as the temporal dose variation from fraction to fraction in a fractioned radiation therapy schedule.

To help ensure that target tissue 50 will be irradiated for at least some time when the radiation is delivered to an area of motion envelope 54 (e.g., subfield 52), the dose rate may be decreased and the dose delivery time may be increased. For example, if the irradiated subfield 52 occupies a small portion of motion envelope 54 of target tissue 50, a complete breathing cycle takes approximately 4 seconds, and 0.05 Gray/second of radiation is delivered over 1 second, the target tissue may not occupy the subfield during therapy delivery if gating is not used. Adjusting the dose rate to deliver 0.01 Gray/second over 4 seconds may help ensure that the target tissue occupies the irradiated subfield 52 during therapy delivery. By lowering the dose rate, a complete hit or miss of target tissue 50 may be avoided, which would narrow the possible dose distributions that may be delivered for a given subfield or a set of subfields. Consequently, the temporal dose variation may be decreased.

Figure 6A:
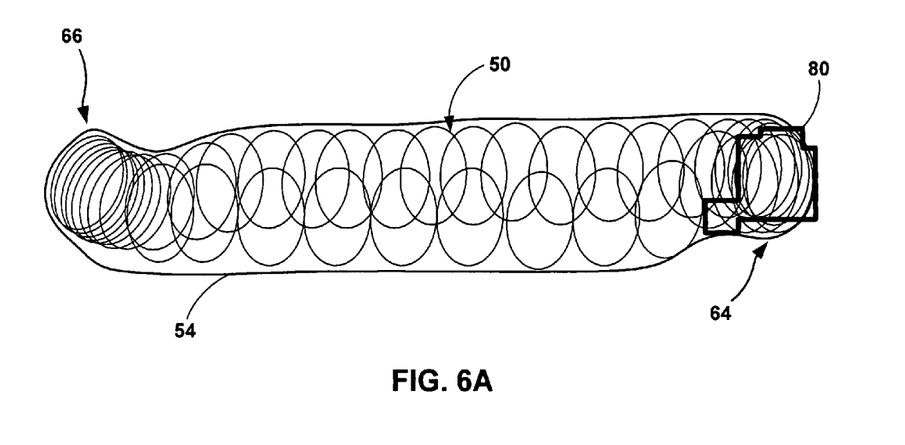
FIG. 6A is a schematic diagram of an example treatment subfield defined using another example MLC configuration.
Figure 6B:
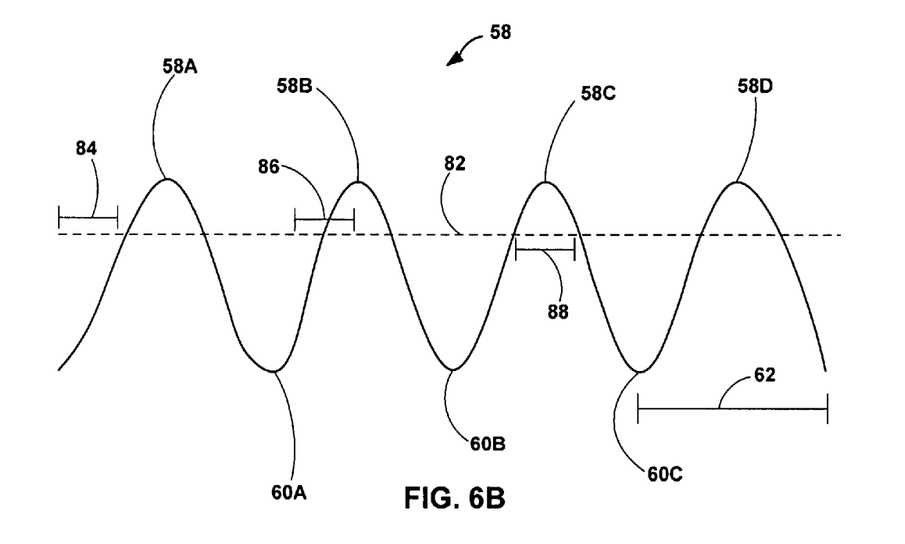
FIG. 6B is a graph of the patient's breathing pattern associated with the target tissue's motion envelope.

FIGS. 6A and 6B further illustrate the effects of dose rate adjustment. FIG. 6A is a schematic view of example subfield 80 of treatment field 15 (FIG. 1) formed using another example MLC 18 configuration, and FIG. 6B is a graph of the patient's breathing pattern 58 associated with the target tissue's motion envelope 54. Since subfield 80 occupies a small portion of motion envelope 54, and in the example shown in FIG. 6A, target tissue 50 only occupies subfield 80 when patient 16 is at or near a substantially full inhale. As FIGS. 6A and 6B illustrate, target tissue 50 only occupies subfield 80 when the phase of the patient's breathing is above threshold 82 (i.e., between threshold 82 and peaks 59). Using the standard dose rate, therapy delivery to subfield 80 may occur for only a fraction of the breathing cycle (e.g., breathing cycle 62), and the dose delivered to target tissue 50 may be dependent on which phase of the breathing cycle patient 16 is in when therapy delivery is initiated.

Intervals 84, 86, and 88 illustrate examples of how the dose to target tissue 50 may vary based on when therapy delivery is started. In the illustrated example, using the standard dose rate (e.g., 0.05 Gray/second), therapy is delivered to patient 16 during approximately one third of the breathing cycle. If therapy delivery is started when patient 16 begins to inhale, as illustrated by interval 84, target tissue 50 may be completely missed. As interval 86 illustrates, target tissue 50 may be partially hit and missed if therapy delivery is started when patient 16 is further into the inhale process. Finally, as illustrated by interval 88, target tissue 50 may be completely hit by radiation beam 10 if therapy delivery is started when patient 16 is even further along in the inhale process.

To help ensure that target tissue 50 will be irradiated for at least some time when the radiation is delivered to subfield 80, while still maintaining a safe level of radiation dose, the dose rate may be decreased. For example, in the illustrated embodiment, therapy is delivered for approximately one third of the breathing cycle using the standard dose rate. Adjusting the dose rate to deliver therapy at one third strength over a three times longer time interval (e.g., such that therapy is delivered for approximately one complete breathing cycle) may help ensure that target tissue 50 occupies subfield 80 during therapy delivery. By lowering the dose rate, a complete miss of target tissue 50 may be avoided and, consequently, the temporal dose variation between fractions may be decreased. Also, decreasing the dose rate and increasing the delivery time by the same factor ensures that substantially the same total dose is delivered to patient 16 despite the lower dose rate.

The use of the dose rate adjustment module 31 of virtual 4D treatment suite 24 may be based on the fraction of the breathing cycle (e.g., breathing cycle 62) that target tissue 50 occupies the irradiated subfield 80 and the delivery time of radiation to subfield 80. In one embodiment, if the delivery time of radiation to subfield 80 is less than a threshold value, for example approximately 65% of the duration of the breathing cycle, dose rate adjustment module 31 may decrease the dose rate and increase the radiation delivery time. Processor 28 and/or dose rate adjustment module 31 may determine the fraction of the breathing cycle that target tissue 50 occupies the irradiated subfield 80 based on a probability density function. If subfield 80 occupies a large portion of the target tissue's motion envelope 54 and/or target tissue 50 occupies the irradiated volume during a large portion of the breathing cycle, dose rate adjustment module 31 may not adjust the dose rate. However, if the dose rate adjustment module 31 determines that the probability that target tissue 50 will occupy a portion of the treatment field during therapy delivery is less than a given threshold (e.g., substantially less than one), dose rate adjustment module 31 may decrease the dose rate, e.g., such that radiation is delivered for the duration of the breathing period, to ensure that target tissue 50 receives some radiation. Decreasing the dose rate may also increase the temporal dose uniformity from fraction to fraction.

In some embodiments, dose rate adjustment module 31 may adjust the dose rate delivered by radiation system 8 (FIG. 1) such that the delivery time is an integer multiple of the breathing cycle duration. Delivering therapy for a complete breathing cycle or multiples thereof may reduce the temporal dose variation from fraction to fraction. In other embodiments, the dose rate may be reduced by any suitable method in order to comply with constraints set for the expected dose, temporal dose variation, delivery time and/or other relevant parameters set by the practitioner, either manually or with the aid of the 4D treatment suite 24 (FIG. 3).

In other embodiments, dose rate adjustment module 31 may increase the dose rate to decrease delivery time. For example, if target tissue 50 occupies the irradiated volume during a large portion of the breathing cycle, dose rate adjustment module 31 may increase the dose rate to decrease delivery time. The dose rate may also be increased when treatment plan 36 is gated to help negate any possible delivery time increases attributable to delivering therapy during a portion of the breathing cycle if the increased dose rate does not adversely affect the expected dose to the target tissue or associated temporal dose variation. In some cases, increasing the dose rate may be undesirable because the dose delivered to critical structures may also inadvertently be increased. However, as previously described, gating may help increase the probability that radiation beam 10 (FIG. 1) will contact target tissue 50 and decrease the probability that radiation beam 10 will contact critical structures. Thus, with the aid of gating techniques implemented via gating module 29, dose rate adjustment module 31 may increase the dose rate without adversely affecting critical structures. Additional dose rate adjustments (e.g., increases and/or decreases in dose rate) may also be used in combination with gating if further temporal dose variation reduction is desired.

Figure 7:
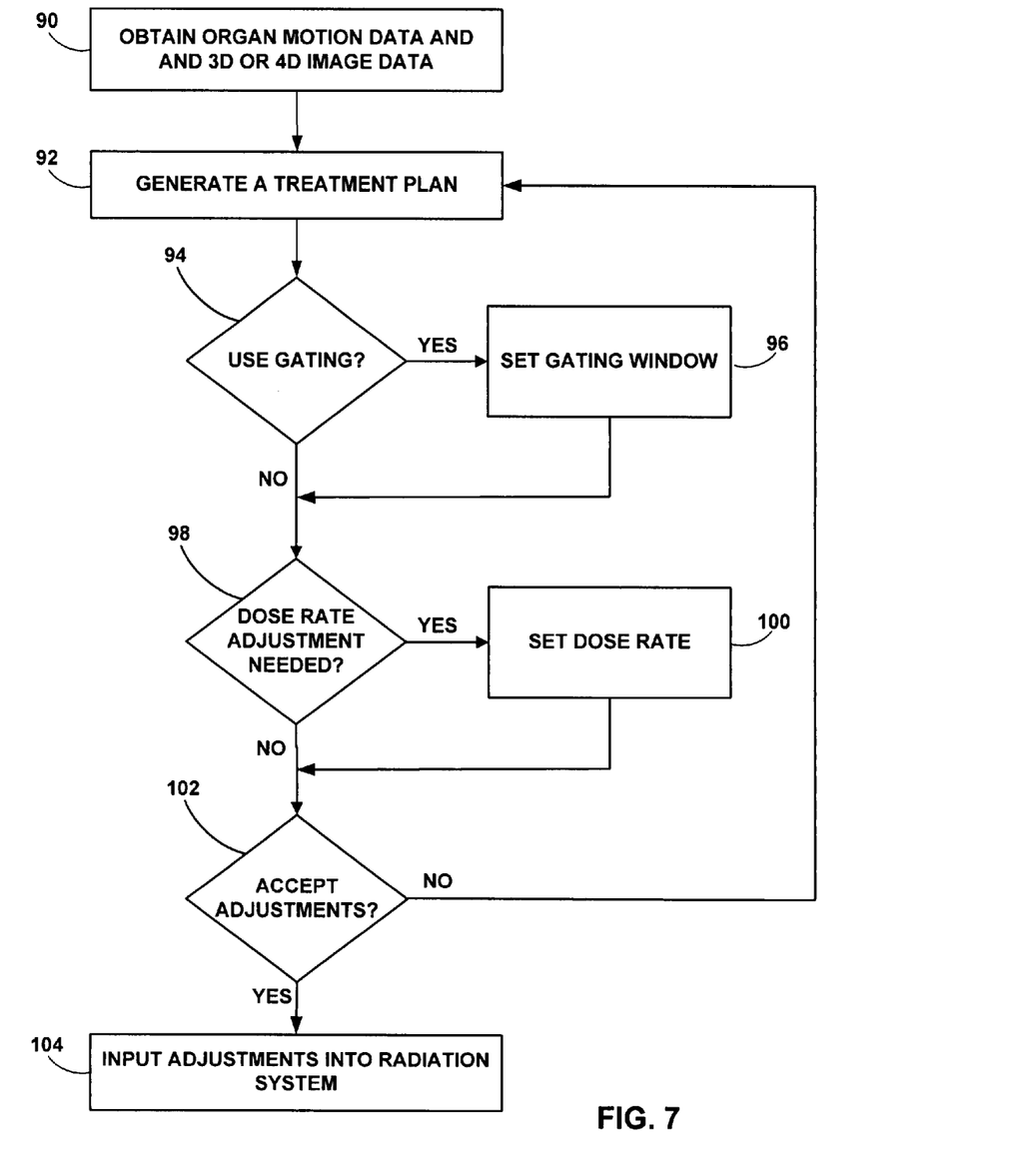
FIG. 7 is a flow diagram illustrating an example method of implementing a virtual 4D treatment suite.

FIG. 7 is a flow chart illustrating an example method of implementing the virtual 4D treatment suite. 4D image data 38 and organ motion data 40 may be obtained (90). Practitioner 44 may generate a treatment plan 36 using a treatment planning system, such as the software described above with respect to FIG. 1, (92) and perform the virtual 4D motion simulation to determine whether gating and/or dose rate adjustment is useful for treatment delivery. For example, with the aid of gating module 29, practitioner 44 may experiment with different gating settings, and radiation dose calculation module 33 may determine the respective expected therapy dose and temporal dose variation values for each of the gating settings and as well as ungated delivery. Based on the expected therapy dose and temporal dose variation values from dose calculation module 33, practitioner 44 may determine whether or not to implement gating with treatment plan 36 (94).

If gating is used, practitioner 44 may interact with gating module 29 of 4D treatment suite 24 to set the gating window based on expected dose, temporal dose variation, and/or treatment time values provided by the virtual 4D treatment suite 24 (96). Alternatively, gating module 29 may automatically set the gating window or provide a starting gating window, which practitioner 44 may modify by interacting with the gating window via user interface 26 of virtual 4D treatment suite 24. In some embodiments, one gating window is set for the entire treatment plan. In other embodiments, multiple subfield-specific gating windows may be determined.

Next, practitioner 44 with the aid of dose rate adjustment module 31 may determine if dose rate adjustment is necessary (98). For example, if gating is not used and target tissue 50 only occupies the irradiated subfield for a portion of the breathing cycle, the dose rate may be adjusted to ensure that at least some dose is delivered to target tissue 50. As a further example, dose rate adjustments may be used in combination with gating if further temporal dose variation reduction is desired. Alternatively, dose rate adjustment module 31 may automatically determine whether dose rate adjustment is necessary or provide a recommendation to practitioner 44 (98). If dose rate adjustments are necessary, practitioner 44 may interact with dose rate adjustment module 31 to set the dose rate (100). Dose and temporal dose variation values for possible dose rates may be provided by dose calculation module 33 to aid in setting the dose rate. Alternatively, dose rate adjustment module 31 may automatically set the dose rate or recommend a dose rate to practitioner (100). Other therapy constraints, such as delivery time, may also be considered. In some embodiments, each subfield of the treatment plan is analyzed. In other embodiments, a user may select to analyze only some of the subfields of the treatment plan. Additionally, in other embodiments; only one of gating or dose rate analysis may be performed.

Practitioner 44 may decide whether or not to accept proposed gating and/or dose rate adjustments (FIG. 1) (102). If practitioner 44 accepts the proposed adjustments, the adjustments may be inputted into radiation system 8 (FIG. 1) or otherwise store the proposed gating and/or dose rate adjustments for later use (104). If practitioner 44 does not accept the proposed changes, a new treatment plan may be generated (92). For example, if, based on the analysis of the virtual 4D simulator, the expected dose to be delivered to the target tissue is substantially lower than the prescribed dose specified in the treatment plan, the treatment plan may be modified.

Using computer modeling, a dose rate adjustment experiment was conducted to calculate a coefficient of variation (CV) in delivered dose, which may be the standard deviation in dose per fraction delivered to at least a portion of the target tissue (e.g., a defined portion of the target tissue or the entire target tissue) for the entire treatment course divided by the average dose per fraction to the same portion of the target tissue (e.g., the defined portion of the target tissue or the entire target tissue). The CV was calculated for three dose profiles: a measured dose profile, a simulated dose profile, and a dose rate override (DRO) simulated dose profile. The results of the computer modeling are shown in Tables 1 and 2 below.

TABLE 1

Calculated Variation in Delivered Dose

| X axis diode | Y axis diode | $CV_{measured}$ | $CV_{simulated}$ | $CV_{DROsimulated}$ |
|---|---|---|---|---|
| 22 | 22 | 2.26% | 0.38% | 0.31% |
| 24 | 22 | 5.95% | 2.70% | 0.32% |
| 21 | 23 | 1.55% | 3.33% | 0.26% |
| 23 | 23 | 0.24% | 0.38% | 0.35% |
| 25 | 23 | 6.55% | 4.78% | 1.34% |
| 22 | 24 | 1.08% | 4.06% | 0.94% |
| 24 | 24 | 4.04% | 6.30% | 0.32% |
| | Average CV | 3.09% | 3.13% | 0.55% |

TABLE 2

Calculated Variation in Delivered Dose

| X axis diode | Y axis diode | $CV_{measured}$ | $CV_{simulated}$ | $CV_{DROsimulated}$ |
|---|---|---|---|---|
| 19 | 21 | 10.33% | 17.0% | 4.8% |
| 21 | 21 | 1.42% | 0.0% | 0.0% |
| 23 | 21 | 3.73% | 4.9% | 0.5% |
| 18 | 22 | 21.75% | 60.4% | 18.1% |
| 20 | 22 | 7.47% | 17.3% | 5.5% |
| 22 | 22 | 0.47% | 0.0% | 0.0% |
| 24 | 22 | 3.38% | 4.9% | 0.5% |
| 21 | 23 | 3.54% | 6.3% | 3.6% |
| 23 | 23 | 0.59% | 0.0% | 0.0% |
| 25 | 23 | 6.87% | 13.4% | 1.1% |
| 22 | 24 | 4.20% | 6.3% | 3.6% |
| 24 | 24 | 1.33% | 0.0% | 0.0% |
| 26 | 24 | 8.69% | 7.1% | 2.6% |
| 23 | 25 | 1.42% | 0.0% | 0.0% |
| 25 | 25 | 6.90% | 6.3% | 0.9% |
| | Average CV | 5.47% | 9.6% | 2.7% |

The measured dose profile ($CV_{measured}$) was obtained using a diode array at an approximately 5 centimeter equivalent depth in water attached to a robotic apparatus to mimic tumor motion. Both the simulated dose profile ($CV_{simulated}$) and the dose rate override simulation profile ($CV_{DROsimulated}$) were computed using a computer program based on the Visual Basic programming language. The variation of measurement points (i.e., the arrangement of virtual measurement points) in the computer simulation were generated in a manner to correlate with the physical measurement points for the robotic diode array apparatus. The calculated variation for a first beam profile is shown in Table 1, and the calculated variation for a second beam profile is shown in Table 2. For both the first and second beam profiles, the dose rate was decreased when the delivery time for a subfield was less than sixty-five percent of the breathing period (i.e., the time to complete one full breathing cycle). The threshold value of sixty-five percent was merely selected as one example threshold. The threshold value is not limited to sixty-five percent.

The first beam profile included five subfields, and the delivery time for three out of the five subfields was less than sixty-five percent of the breathing period. For the dose rate override simulated profile, the delivery time was increased by a factor of three and the dose rate was decreased by a factor of three for the three subfields with delivery times of less than sixty-five percent of the breathing period prior to the dose rate adjustment. In the example illustrated in Table 2, the beam profile included ten subfields, and the delivery time for each of the ten subfields was less than sixty-five percent of the breathing period. Therefore, the dose rate was decreased by a factor of three for all ten subfields to obtain the dose rate override simulation profile. The computer modeling results shown in Tables 1 and 2 suggest that a decrease in temporal dose variation between the simulated dose profiles and the simulated dose rate override dose profiles.

Additionally, Tables 1 and 2 suggest that diode pairs with high (or low) temporal dose variation tend to have relatively high (or low) variation among all three of the different dose profiles. For example, x-axis diode 25 and y-axis diode 23 of Table 1 exhibited a high temporal dose variation among all three dose profiles. The calculated variations for x-axis diode 25 and y-axis diode 23 of Table 1 for the measured dose profile were among the highest of all the calculated variations for the measured dose profile of Table 1. Likewise, the calculated variations for x-axis diode 25 and y-axis diode 23 for the simulated dose profile and the simulated dose rate optimized profiles were among the highest of all the calculated variations for their respective dose profiles. In this manner, there is a general agreement between all three dose profiles.

In one or more exemplary embodiments, various functions described in this disclosure may be implemented in hardware, software, and/or firmware, or any combination thereof. If implemented in hardware, the functions may be implemented in a processor. A processor may include one or more microprocessors, microcontrollers, digital signal processors (DSPs), application specific integrated circuits (ASICs), field programmable gate arrays (FPGAs), or the like. Such components may reside within a computing system or other systems. If implemented in software, the functions may be stored as one or more instructions or code on a computer-readable medium.

Computer-readable media includes computer storage media. A storage medium may be any available media that can be accessed by a computer. By way of example, and not limitation, such computer-readable media can comprise random-access memory (RAM), read-only memory (ROM), electrically-erasable programmable read-only memory (EEPROM), compact disc read-only memory (CD-ROM) or other optical disk storage, magnetic disk storage or other magnetic storage devices, or any other medium that can be used to store desired program code in the form of instructions or data structures and that can be accessed by a computer. Storage media may comprise computer program products. Disk and disc, as used herein, includes compact disc (CD), laser disc, optical disc, DVD optical discs, floppy disk and blu-ray disc where disks usually reproduce data magnetically, while discs reproduce data optically with lasers. Combinations of the above should also be included within the scope of computer-readable media.

Various embodiments of the invention have been described. Although virtual 4D treatment suite 24 of FIG. 3 is shown to have a single processor 28 that controls, among other things, gating module 29, dose rate adjustment module 31, and dose calculation module 33, in other embodiments, at least one of gating module 29, dose rate adjustment module 31, and dose calculation module may include its own processor that operates independently of the other modules 29, 31, 33 or processor 28, or operates in conjunction with the processor of at least one of modules 29, 31, 33 or processor 28. Other configurations of virtual 4D treatment suite 24 are also contemplated. These and other embodiments are within the scope of the following claims.

The invention claimed is:

1. A method comprising:
   identifying relative motion between a region of interest of a patient and at least a portion of a treatment field defined by a proposed treatment plan;
   calculating an expected therapy dose and an associated temporal variation in the expected therapy dose to be delivered to the region of interest for the proposed treatment plan based on the identified relative motion between the region of interest and the at least the portion of the treatment field; and
   determining whether to apply a dose management technique to the proposed treatment plan based on the expected therapy dose and the associated temporal variation in the expected therapy dose.

2. The method of claim 1, wherein the dose management technique comprises at least one of gating or dose rate adjustment.

3. The method of claim 2, further comprising setting a gating window.

4. The method of claim 3, wherein setting the gating window comprises comparing two or more potential gating windows.

5. The method of claim 2, further comprising adjusting a dose rate based on the expected therapy dose and the associated temporal variation in the expected therapy dose.

6. The method of claim 5, wherein adjusting the dose rate comprises comparing two or more potential dose rates.

7. The method of claim 5, further comprising adjusting a dose delivery time based on the expected therapy dose and the associated temporal variation in the expected therapy dose.

8. The method of claim 7, wherein adjusting the dose rate comprises decreasing the dose rate and adjusting the dose delivery time comprises increasing the dose delivery time.

9. The method of claim 1, further comprising generating the treatment plan based on a 4D image data set of the region of interest of the patient.

10. The method of claim 1, wherein the treatment plan comprises a dose to be delivered to the patient.

11. The method of claim 1, wherein the region of interest comprises at least one of a target tissue or a critical structure.

12. The method of claim 1, wherein identifying the relative motion between the region of interest and the at least the portion of the treatment field comprises identifying a movement of the region of interest throughout a breathing cycle of the patient.

13. The method of claim 1, wherein identifying relative motion between the region of interest and the at least the portion of the treatment field comprises obtaining an image data set of the patient.

14. The method of claim 1, wherein the treatment field comprises a radiation treatment field.

15. A system comprising:
   a dose calculation module that calculates an expected therapy dose and an associated temporal variation in the expected therapy dose to be delivered to a region of interest for a proposed radiation therapy treatment plan for a patient based on an identified relative motion between the region of interest and at least a portion of a treatment field; and
   a dose management module that determines whether to implement a dose management technique based on the expected therapy dose and the associated temporal variation in the expected therapy dose.

16. The system of claim 15, further comprising a treatment planning system that generates the proposed treatment plan, wherein the region of interest and the treatment field are based on the treatment plan.

17. The system of claim 15, wherein the system further comprises a database including at least one of the treatment plan, breathing data of the patient, 4D image data of the region of interest, patient data or dosimetric constraint rules.

18. The system of claim 15, wherein the dose management module comprises a gating module that selects a gating window for the treatment plan based on the identified relative motion between the region of interest and the at least a portion of the treatment field, wherein the dose calculation module determines the expected therapy dose and the associated temporal variation in the expected therapy dose based on the gating window.

19. The system of claim 18, further comprising a user interface, wherein the gating module selects a gating window for the treatment plan based on user input received via the user interface.

20. The system of claim 15, wherein the dose management module comprises a dose rate adjustment module that adjusts a dose rate of the treatment plan based on the identified relative motion between the region of interest and the at least a portion of the treatment field.

21. The system of claim 20, wherein the expected therapy dose comprises a first expected therapy dose, and wherein the dose calculation module determines a second expected therapy dose and an associated temporal variation in the second expected therapy dose based on the adjusted dose rate.

22. The system of claim 15, further comprising a processor that identifies the relative motion between the region of interest and the at least a portion of a treatment field throughout a breathing cycle of the patient.

23. A computer-readable medium comprising instructions for causing a programmable processor to:
   identify relative motion between a region of interest and at least a portion of a treatment field defined by a proposed treatment plan;
   calculate an expected therapy dose and an associated temporal variation in the expected therapy dose to be delivered to the region of interest for the proposed treatment plan based on the identified relative motion between the region of interest and the at least the portion of the treatment field; and determine whether to apply a dose management technique to the proposed treatment plan based on the expected therapy dose and the associated temporal variation in the expected therapy dose.

24. The computer-readable medium of claim 23, wherein the dose management technique comprises at least one of gating or dose rate adjustment.

25. A system comprising:
means for identifying relative motion between a region of interest of a patient and at least a portion of a treatment field defined by a proposed treatment plan;
means for calculating an expected therapy dose and an associated temporal variation in the expected therapy dose to be delivered to the region of interest for the proposed treatment plan based on the identified relative motion between the region of interest and the at least the portion of the treatment field; and
means for determining whether to apply a dose management technique to the proposed treatment plan based on the expected therapy dose and the associated temporal variation in the expected therapy dose.

26. The system of claim 25, wherein the dose management technique comprises at least one of gating or dose rate adjustment.

* * * * *

UNITED STATES PATENT AND TRADEMARK OFFICE
CERTIFICATE OF CORRECTION

PATENT NO. : 7,551,717 B2
APPLICATION NO. : 11/894378
DATED : June 23, 2009
INVENTOR(S) : Wolfgang Axel Tomé et al.

It is certified that error appears in the above-identified patent and that said Letters Patent is hereby corrected as shown below:

Title Page, Item (75) Inventors: Wolfgang Axel Tomé, Madison, WI (US); Eric Drew Ehler, Madison, WI (US); should be --Inventors: Wolfgang Axel Tomé, Madison, WI (US); Eric Drew Ehler, Madison, WI (US); Karl Bzdusek, Fitchburg, WI (US)--

Signed and Sealed this

Twenty-ninth Day of June, 2010

David J. Kappos
*Director of the United States Patent and Trademark Office*